United States Patent [19]

Hata et al.

[11] Patent Number: 5,344,850
[45] Date of Patent: Sep. 6, 1994

[54] TOPICAL COMPOSITION FOR PREVENTING OR TREATING ACNE VULGARIS

[76] Inventors: Hamako Hata, 3-1, Urashibata-cho, Wakabayashi-ku, Sendai-shi, Miyagi; Kenya Ishida; Toshiya Sato, both of c/o Takasago International Corporation, Central Research Laboratory, 36-31, Kamata 5-chome, Ohta-ku, Tokyo, all of Japan

[73] Assignee: Takasago International Corporation, Japan

[21] Appl. No.: 82,855

[22] Filed: Jun. 28, 1993

[30] Foreign Application Priority Data

Jun. 29, 1992 [JP] Japan .................................. 4-171163

[51] Int. Cl.$^5$ .............................................. A61K 31/045
[52] U.S. Cl. ...................................... 514/739; 514/724
[58] Field of Search ............................... 514/739, 724

[56] References Cited

U.S. PATENT DOCUMENTS 4,220,665  9/1980  Klein ...................................... 424/343
4,921,694  5/1990  Hoppe et al. .......................... 424/65

OTHER PUBLICATIONS

English translation of JP-A-3-279318, (Dec. 10, 1991).

Partial English translation of JP-A-57-128612 (with copy of JP-A-57-128612 attached), (Aug. 10, 1982).

*Primary Examiner*—Zohreh Fay
*Attorney, Agent, or Firm*—Sughrue, Mion, Zinn, Macpeak, & Seas

[57] ABSTRACT

A topical composition for treating or preventing acne vulgaris which comprises at least one saturated or unsaturated chain alcohol having 18 carbon atoms represented by formula (1):

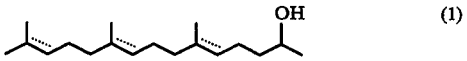

(1)

wherein a dotted line represents either the presence or the absence of a double bond as an active ingredient, makes it possible to inhibit proliferation of *Propionibacterium acnes,* which causes acne vulgaris, or kill the bacterium to effectively treat or prevent acne vulgaris. The compound represented by formula (1) can be easily synthesized and has an extremely low toxicity. Furthermore, it exerts an excellent antibacterial effect on *Propionibacterium acnes* even when used at a relatively low concentration. Thus it can be used only in a small amount, which ensures a high safety.

6 Claims, No Drawings

TOPICAL COMPOSITION FOR PREVENTING OR TREATING ACNE VULGARIS

FIELD OF THE INVENTION

This invention relates to a topical composition for treating or preventing acne vulgaris. More particularly, it relates to a topical composition for treating or preventing acne vulgaris which comprises, as an active ingredient, a saturated or unsaturated chain alcohol having 18 carbon atoms and which inhibits proliferation of *Propionibacterium acnes* which is a bacterium causing acne vulgaris or kills the bacterium.

BACKGROUND OF THE INVENTION

Acne vulgaris is a skin disease, of mainly youths, involving comedos, papulae and pustules appearing on the face, the center of the chest or the upper part of the back. Main causes of ache vulgaris include (1) hypersteatosis; (2) stricture of hair-follicles; and (3) proliferation of *Propionibacterium acnes*, which is one of the gram-positive anaerobic bacteria, in the pilosebaceous gland.

Attempts have been made to treat acne vulgaris by mainly focusing on the removal of the above-mentioned three causes. For example, female hormones are used for suppressing hypersteatosis, keratolytic substances, such as salicylic acid and resorcin, are used to eliminate stricture of hair-follicles, and bactericidal disinfectants, such as chlorohexidine gluconate, are used for inhibiting proliferation of the bacterium.

However, conventionally employed bactericidal disinfectants inherently cause erythema and peeling and thus irritate the skin by, for example, seriously roughening the skin. Therefore, the allowable doses of such bacteriocides are restricted, which makes it difficult to fully obtain their effects.

In recent years, there has been proposed to use various natural substances and synthetic compounds, which have antibacterial activity and safety for the skin, for treating acne vulgaris. For example, it has been proposed to use antibacterial substances originating from natural materials such as ferruginol (JP-A-1-311018; the term "JP-A" as used herein means an "unexamined published Japanese patent application"), totarol (JP-A-1-311019), sempervirol (JP-A-1-311020), tetrahydroabietic acid and esters thereof (JP-A-2-188513), and anacardic acid (JP-A-4-36238) for treating ache vulgaris. Further, it has been proposed to use synthetic compounds such as a composition comprising a 4-n-butyl catechol derivative together with a heavy metal [International Patent Laid-Open No. 88/03806 (1988)] and 1-hydroxy-2-pyridone [U.S. Pat. No. 4,762,847 (1988)] as an antibacterial component for treating acne vulgaris.

Among these substances, those originating from natural materials occur in a small amount in nature and, therefore, cannot be fully utilized industrially. On the other hand, the synthetic compounds cannot be easily synthesized. In order to use these synthetic compounds as a drug for treating acne vulgaris, it is needed to add a heavy metal to the drug, which results in some fear for human health and, furthermore, requires care for the environmental pollution upon disposal. Accordingly, these compounds are not satisfactory as an active ingredient of a drug for treating acne vulgaris.

The saturated or unsaturated chain alcohol having 18 carbon atoms represented by formula (1)

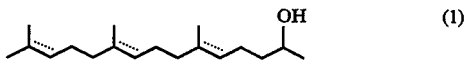

wherein a dotted line represents either the presence or the absence of a double bond, which is an active ingredient of the topical composition for treating or preventing acne vulgaris according to the present invention, can be easily synthesized from geranyl acetone which has been used as an intermediate for synthesizing drugs. This compound is available at a relatively low cost. Although it has been proposed to use this compound for eliminating harmful aquatics (JP-A-57-128612), it has neither been reported that this compound is effective for inhibiting proliferation of *Propionibacterium acnes* causing acne vulgaris or killing the bacterium nor that it has an antibacterial activity.

JP-A-3-279318 proposes a topical composition which comprises a drug for treating acne and a surfactant having an aliphatic alcohol residue skeleton containing one or more unsaturated bonds which conceptually involves the compound represented by formula (1). However, the aliphatic alcohols disclosed therein are compounds such as oleyl alcohol and none of the compounds represented by formula (1) used in the present invention is particularly disclosed therein. Namely, the aliphatic alcohols disclosed therein are employed exclusively as a surfactant and there is no description relating to the antibacterial activity of these compounds.

It is also known that farnesol (3,7,11-trimethyl-dodeca-2,6,10-trien-1-ol) and dehydronerolidol (3,7,11-trimethyldodeca-6,10-dien-1-yn-3-ol), each having a skeleton similar to that of the compound represented by formula (1), can inhibit the growth of *Staphylococcus aureus*, *Bacillus subtilis*, *Escherichia coli*, *Sarcina lutea*, *Corynebacterium equi*, *Mycobacterium avium*, *Mycobacterium phlei*, *Nocardia asteroides* and *Aerobacter aerogenes* at a concentration of from 15.6 ppm to 1000 ppm (JP-A-53-91122). Thus it has been proposed to use these compounds as an agricultural/horticultural bactericide (JP-A-56-73002). In particular, it is known that farnesol exhibits a growth inhibitory effect on *Staphylococcus epidermidis*, *Pseudomonas aeruginosa*, *Corynebacterium species*, *Aerobacter kleps* and *Candida albicans* causing the smell of sweat in addition to the bacteria as cited above (JP-A-54-11235 corresponding to U.S. Pat. No. 4,220,665 and British Patent No. 2000030; and JP-A-60-64913 corresponding to EP 126944 and DE 3315058). Thus there have been proposed a deodorant and antibacterial composition to be used in cosmetics or preparations for topical use which comprise farnesol blended with phenyl hydroxyalkyl ether and glycerol monolaurate at a specific ratio (JP-A-64-22815 corresponding to U.S. Pat No. 4,921,694 and EP 297310).

However each of the compounds described in these publications differs from the compound represented by formula (1) used in the present invention in being a primary alcohol, having a triple bond or having a carbon chain of different length. Further, no description relating to the antibacterial activity on *Propionibacterium acnes* is given in these publications, except that JP-A-64-22815 teaches that farnesol shows little activity when used alone but exhibits an antibacterial activity when used in combination with phenyl hydroxyalkyl ether and glycerol monolaurate.

SUMMARY OF THE INVENTION

An object of the present invention is to provide a novel topical composition for treating or preventing acne vulgaris comprising an antibacterial component which is safe for the skin, can be easily synthesized, is available at a low cost, and has an excellent therapeutic effect on acne vulgaris.

In order to achieve this object, the present inventors have paid their attention to chain isoprenoid which has been used in, for example, antiulcer drugs, and is known as a safe compound for man. In general, chain alcohols have more or less antibacterial activity. It has been reported that a chain alcohol having 12 carbon atoms has the highest antibacterial effect which is gradually lowered with a decrease or increase in carbon atom number [Nobuyuki KATO et al., J. Antibact. Antifung. Agents, 8(8), pp. 325-331 (1980)].

Considering the fact that *Propionibacterium acnes* prefers a fatty environment, the present inventors have synthesized various compounds having longer carbon chains than farnesol and dehydronerolidol which have been known to have antibacterial activities against some bacteria and determined the antibacterial activities against *Propionibacterium acnes*. As a result, it has been found that a saturated or unsaturated chain alcohol having 18 carbon atoms represented by formula (1), which can be easily synthesized from geranyl acetone employed as an intermediate for synthesizing drugs, has an intense antibacterial activity against *Propionibacterium aches* and an extremely low toxicity.

Accordingly, the present invention relates to a topical composition for treating or preventing acne vulgaris which comprises, as an active ingredient in an amount effective to inhibit proliferation of *Propionibacterium acnes*, at least one saturated or unsaturated chain alcohol having 18 carbon atoms represented by formula (1):

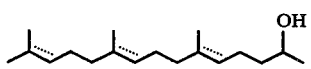
(1)

wherein a dotted line represents either the presence or the absence of a double bond, and at least one carrier or diluent acceptable for topical application.

DETAILED DESCRIPTION OF THE INVENTION

The topical composition according to the present invention can be arbitrarily formulated into any dose form, such as cosmetic lotions, emulsions, creams, packs, aqueous ointments or oily ointments, and is widely usable as, for example, drugs, quasi drugs, cosmetics and sanitary products.

Particular examples of the compound represented by formula (1) [hereinafter referred to as compound(s) (1)], i.e., the active ingredient, include 6,10,14-trimethyl-pentadecan-2-ol [the compound of formula (2) as specified in the following reaction scheme, hereinafter referred to as compound (2) and the same definition shall apply to the other compounds], 6,10,14-trimethyl-5,9,13-pentadecatrien-2-ol [the compound represented by formula (3) as specified in the following reaction scheme], 6,10,14-trimethyl-5,9-pentadecadien-2-ol, 6,10,14-trimethyl-5,13-pentadecadien-2-ol, 6,10,14-trimethyl-9,13-pentadecadien-2-ol, 6,10,14-trimethyl-5-pentadecen-2-ol, 6,10,14-trimethyl-9-pentadecen-2-ol and 6,10,14-trimethyl-13-pentadecen-2-ol. Each of these compounds has asymmetric carbon atom(s) and/or double bond(s) and occurs as stereoisomers. All of these isomers are usable in the present invention. Either one of these compounds or a mixture comprising two or more of them may be used. Furthermore, both synthetic compounds and products extracted and purified from natural materials are usable. For example, 6,10-14-trimethylpentadecan-2-ol [compound (2)], which is one of the compounds of formula (1), is reported as a component of a moth pheromone [Chemical Abstracts, 107, 151532d (1987)]. On the other hand, it can be synthesized by using geranyl acetone [compound (4) as specified in the following reaction scheme] or nerolidol [compound (5) as specified in the following reaction scheme] as a starting compound in accordance with the following reaction scheme [compound (4)→compound (5)→compound (6)→compound (3)→compound (2)] [Yoshiji FUJITA et al., Yuki Gosei Kagaku (Organic Synthetic Chemistry), 37(3), pp. 224-239 (1979)]. Besides, the compounds of formula (1) having 0 to 3 double bond(s) can be obtained in the form of a mixture thereof in accordance with the following reaction scheme except for controlling the amount of hydrogen to be absorbed in the step of hydrogenation from the compound (3) to the compound (2). The thus obtained mixture can be used in the composition of the present invention as it is.

Reaction scheme

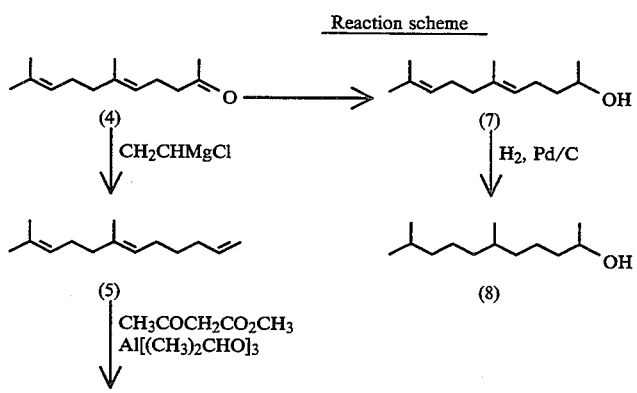

Reaction scheme
-continued

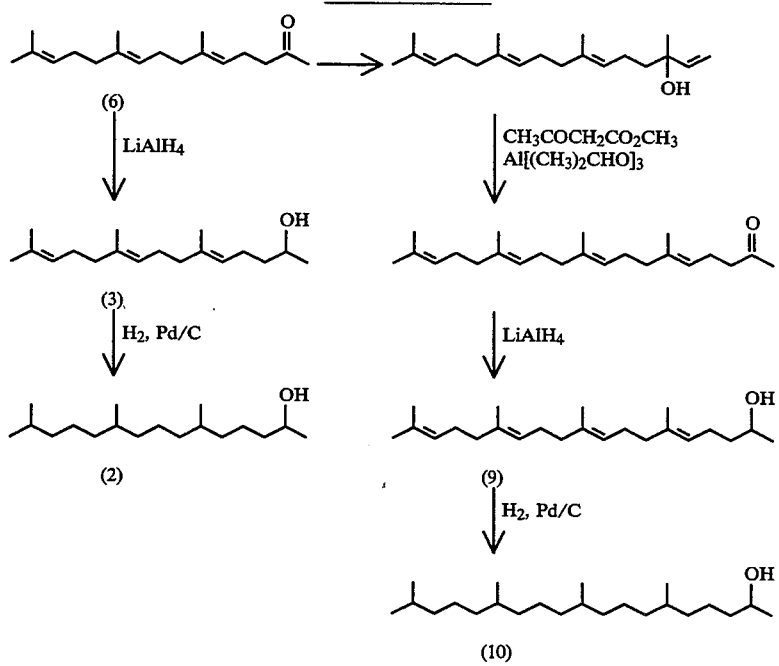

However, a natural material contains the desired active component only in an extremely small amount. Therefore, the use of such a component extracted and purified from a natural material as an active ingredient of the topical composition for treating or preventing acne vulgaris of the present invention suffers from economical problems and a disadvantage in production efficiency. Accordingly, it is preferable to use a synthetic compound as an active ingredient of the topical composition for treating or preventing acne vulgaris of the present invention, so long as it causes no particular problems during the production process. It is particularly preferable to use the above-mentioned 6,10,14-trimethylpentadecan-2-ol [compound (2)] and 6,10,14-trimethyl-5,9,13-pentadecantrien-2-ol [compound (3)] as the active ingredient, since these compounds can be easily synthesized.

As shown in the above reaction scheme, alcohols having a shorter carbon chain, compound (7) or (8), and those having a longer carbon chain, compound (9) or (10), derived from the same starting material, compound (4), are also synthesized and their antibacterial activities against *Propionibacterium acnes* are examined. When compared with the antibacterial activities of compounds (2) and (3) which are the active ingredient of the present invention, compounds (7) to (10) each shows a minimum growth inhibitory concentration (MIC) of about 25 to 50 μg/ml which is higher than those of compounds (2) and (3) (i.e., 1.56 to 3.13 μg/ml) as shown in Test Example 1 as given hereinafter. It is thus proved that the compounds (7) to (10) are inferior in antibacterial activity to the compounds (2) and (3).

Compound (1) shows its effect in an amount of about 0.005 % by weight when it is contained in a topical composition for preventing and treating acne vulgaris. Its effect is sufficiently exerted in an amount of about 0.5% by weight. Accordingly, the amount of compound (1) ranges from about 0.005 to 0.5% by weight, preferably about 0.01 to 0.5% by weight, based on the total weight of the composition.

In addition to the above-mentioned active ingredient, the topical composition for treating or preventing acne vulgaris according to the present invention may appropriately contain various components commonly employed for topical compositions, such as surfactants, humectants, lower alcohols, water, thickeners, oil bases, UV absorbents, perfumes, antioxidants, chelating agents, colorants, antiseptics and antifungal agents, depending on the dose form. It may further contain other active ingredients such as female hormones and salicylic acid.

The topical composition for treating or preventing acne vulgaris according to the present invention thus obtained may be preferably applied to the affected part in an appropriate amount one to three times a day.

The present invention is illustrated in detail below with reference to Production Examples of the active ingredient and Test Example for measuring the antibacterial activity thereof, Formulation Examples of the topical compositions and Test Example for measuring the antibacterial activity of the compositions and Test Example for a therapeutic effect of the compositions on acne vulgaris. However, it is to be understood that the present invention is not restricted thereto.

PRODUCTION EXAMPLE 1

Production of
6,10,14-trimethyl-5,9,13-pentadecatrien-2-ol

[compound (3)]

Nerolidol [compound (5) (manufactured by Takasago International Corporation] to be used as a starting material was subjected to Carroll reaction using acetoacetate in accordance with the method of W. Kimel et al. [J. Org. Chem., 23(2), pp. 153-157 (1958)] to give 6,10,14-trimethyl-5,9,13-pentadecatrien-2-one [compound (6)].

To a 3 liter three-neck flask equipped with a dropping funnel, a stirrer and a condenser were added 38 g of lithium aluminum hydride and 700 ml of ethyl ether in a nitrogen gas stream and the mixture was stirred while maintaining at 0° C. To this solution was added dropwise 262 g (1.0 mol) of compound (6) as obtained above dissolved in 500 ml of ethyl ether within about 1 hour and the mixture was further reacted under stirring at room temperature for about 13 hours. After the completion of the reaction, 380 ml of water and 380 ml of a 15% aqueous solution of sodium hydroxide were added to the reaction mixture. The white crystals thus formed were separated by filtering through 50 g of Celite, extracted with 500 ml of ethyl ether three times and then concentrated after dehydrating with sodium sulfate anhydride. 251 g of the oily substance thus obtained was purified by silica gel column chromatography (silica gel: 1000 g, developing solvent: hexane:ethyl acetate=2:1 by volume). Thus 250 g (yield: 94.7 %) of the target 6,10,14- trimethyl-5,9,13-pentadecatrien-2-ol, compound (3), was obtained.

The physicochemical properties of compound (3) were as follows.

Mass spectrum (MS) (m/e): 264 (M+).

PRODUCTION EXAMPLE 2

Production of 6,10,14-trimethylpentadecan-2-ol [compound (2)]

To a 1 liter round-bottle flask were added 12 g of 5% palladium-carbon, 500 ml of ethanol and 52.8 g of compound (3) as obtained above and hydrogenation was carried out under atmospheric pressure with stirring at room temperature. After confirming that 13.4 l of hydrogen had been absorbed within about 4 hours, the palladium-carbon was removed by filtering through Celite. Then the residue was concentrated and purified by silica gel column chromatography (silica gel: 500 g, development solvent: hexane:ethyl acetate=3:1 by volume). Thus 50.0 g (yield: 92.6 %) of the target 6,10,14-trimethylpentadecan-2-ol, compound (2), was obtained.

The physicochemical properties of compound (2) were as follows.

MS (m/e): 270, 253 (M+ —OH).

Nuclear magnetic resonance spectrum ($^1$H-NMR) (CDCl$_3$)

δ ppm: 0.8-0.9 (12H, m), 1.2 (3H, d, J=6.2 Hz), 1-1.5 (21H, m), 3.75-3.85 (1H, m).

TEST EXAMPLE 1

Antibacteiral activity of compounds (2) and (3)

The minimum growth inhibitory concentrations (MIC) of the compounds (2) and (3) as obtained in Production Examples 1 and 2 on *Propionibacterium acnes* were determined in the following manner.

59.0 g of a GAM (Gifu anaerobic medium) bouillon medium (manufactured by Nissui Pharmaceutical Co., Ltd.) was dissolved in 1 liter of purified water and a test compound was added thereto so as to give a concentration of 100 μg/ml. A serial 2-fold dilution of the mixture thus obtained was made with the medium followed by sterilization. 10 ml portions of the mixture were pipetted into test tubes and each inoculated with 0.1 ml of *Propionibacterium acnes* (ATCC 6919) which had been pre-incubated to give a cell concentration of 1×10$^8$ cells/mi. After stationary incubation under anaerobic conditions for 48 hours, the turbidity was measured at a wavelength of 660 nm. Thus the minimum concentration at which the bacterium did not grow was determined and referred to as MIC. For comparison, MIC of eugenol, which had been known as having a relatively strong antibacterial activity, on *Propionibacterium acnes* was determined. Table 1 shows the results.

TABLE 1

| Test compound | MIC (μg/ml) |
| --- | --- |
| (2) | 3.13 |
| (3) | 1.56 |
| eugenol | 50.0 |

As a result, it has been found that compounds (2) and (3), which are the active ingredient of the present invention, can inhibit proliferation of *Propionibacterium acnes* at an extremely low concentration, as compared with eugenol employed as a comparative compound, and thus have intense antibacterial activity.

Formulation Examples of the compositions comprising compounds (2) and (3) which have been confirmed to have antibacterial activities against *Propionibacterium acnes* are given below.

FORMULATION EXAMPLE 1

| Cosmetic lotion | part by weight |
| --- | --- |
| (1) compound (2) | 0.1 |
| (2) glycerol | 2.0 |
| (3) 1,3-butylene glycol | 2.0 |
| (4) sodium citrate | 0.1 |
| (5) ethanol | 15.0 |
| (6) polyoxyethylene oleyl ether | 0.5 |
| (7) methyl parahydroxybenzoate | 0.1 |
| (8) purified water | the balance |
| total | 100.0. |

The above-mentioned components (1), (5), (6) and (7) were mixed and dissolved at room temperature and then added under stirring to the mixture of the components (2), (3), (4) and (8), which had been similarly mixed and dissolved at room temperature, to give a cosmetic lotion for treating or preventing acne vulgaris.

FORMULATION EXAMPLE 2

Cosmetic lotion

The component (1) of the cosmetic lotion of Formulation Example 1 was replaced by compound (3) and thus a cosmetic lotion for preventing or treating acne vulgaris was obtained.

TEST EXAMPLE 2

Antibacterial activity of the composition

The cosmetic lotions as obtained in Formulation Examples 1 and 2 according to the present invention, a cosmetic lotion containing eugenol instead of the component (1) of Formulation Example 1 (Comparative Example 1) and another cosmetic lotion lacking of the component (1) of Formulation Example 1 (Comparative Example 2) were examined for antibacterial activities against *Propionibacterium acnes*.

A 5.9% aqueous solution of a GAM bouillon medium (manufactured by Nissui Pharmaceutical Co., Ltd.) was sterilized and pipetted into test tubes in 10 ml portions. Then a test cosmetic lotion was added to each test tube to give a concentration of 20 μl/ml and 50 μl/ml. Then, 0.1 ml of the culture of *Propionibacterium acnes* (ATCC 6919), which had been pre-incubated so as to give a cell concentration of 1×10$^8$ cells/ml, was inoculated into the medium in each test tube. After stationary incubation under anaerobic conditions for 48 hours, the turbidity was measured at a wavelength of 660 nm and the growth of the bacterium was observed. Table 2 shows the results.

TABLE 2

| Test cosmetic lotion (active ingredient) | Antibacterial activity | |
|---|---|---|
| | sample conc. 20 μl/ml | sample conc. 50 μl/ml |
| Formulation Example 1 (compound 2) | — | — |
| Formulation Example 2 (compound 3) | — | — |
| Comparative Example 1 (eugenol) | + | ± |
| Comparative Example 2 (none) | ++ | ++ |

—: No growth was observed and the medium remained transparent.
±: Growth was observed a little.
+: Growth was observed and the medium became somewhat turbid.
++: Vigorous growth was observed and the medium became considerably turbid.

As a result, the growth of *Propionibacterium acnes* was scarcely observed in the case of using the cosmetic lotions for treating or preventing acne vulgaris according to the present invention as compared with the case of using the cosmetic lotion of Comparative Example 1 containing eugenol as an active ingredient and that of Comparative Example 2 containing no active ingredient. Thus it has been proved that the compositions of the present the invention have intense antibacterial activities.

| FORMULATION EXAMPLE 3 | |
|---|---|
| Cream | part by weight |
| (1) compound (2) | 0.3 |
| (2) colorant | 0.003 |
| (3) 1,3-butylene glycol | 5.0 |
| (4) yellow beeswax | 2.0 |
| (5) cetanol | 4.0 |
| (6) purified lanolin | 10.0 |
| (7) squalane | 30.0 |
| (8) methyl parahydroxybenzoate | 0.1 |
| (9) polyoxyethylene sorbitan monolaurate | 2.0 |
| (10) purified water | the balance |
| total | 100.0. |

The above component (3) was added to purified water and heated to maintain at 70° C. Thus an aqueous phase was obtained. The component (1) was mixed with the other components and dissolved by heating. The mixture was maintained at 70° C. to give an oily phase. The aqueous phase was added to the oily phase and pre-emulsified. After homogeneously emulsifying in a homo-mixer, an o/w type cream for treating or preventing acne vulgaris was obtained.

| FORMULATION EXAMPLE 4 | |
|---|---|
| Ointment | part by weight |
| (1) compound (2) | 0.2 |
| (2) compound (3) | 0.3 |
| (3) polyethylene glycol 400 | 10.0 |
| (4) liquid paraffin | 12.5 |
| (5) vaseline | 21.0 |
| (6) paraffin | 7.0 |
| (7) glycerol | 49.0 |
| total | 100.0. |

The above components were thoroughly mixed together to give an ointment for treating or preventing acne vulgaris.

| FORMULATION EXAMPLE 5 | |
|---|---|
| Emulsion | part by weight |
| (1) compound (3) | 0.1 |
| (2) liquid paraffin | 10.0 |
| (3) vaseline | 4.0 |
| (4) stearic acid | 2.0 |
| (5) cetanol | 1.0 |
| (6) glyceryl monostearate | 2.0 |
| (7) propylene glycol | 7.0 |
| (8) sodium hydroxide | 0.4 |
| (9) purified water | the balance |
| total | 100.0. |

The above components (1) to (6) were mixed together and dissolved by heating. The mixture was maintained at 70 ° C. to give an oily phase. The other components were mixed, dissolved and heated to 70 ° C. to give an aqueous phase. The aqueous phase was added to the oily phase and homogeneously emulsified in a homo-mixer. Then the mixture was cooled to 30 ° C. under thoroughly stirring to give an emulsion for treating or preventing acne vulgaris.

TEST EXAMPLE 3

Therapeutic effect on acne vulgaris

Control products [the same preparations as those of Formulation Examples 1 to 3 and 5 except lacking of the component (1) or the same preparation as Formulation Example 4 except lacking of the components (1) and (2), namely, compositions consisting of base components] were applied to the left side of the face of 5 subjects suffering from acne vulgaris on the face, while the topical compositions for treating or preventing acne vulgaris obtained in Formulation Examples were applied to the right side thereof, twice a day each in the morning and evening, continuously for 1 month. After 1 month, the therapeutic effects on acne vulgaris were evaluated by comparing the degree of healing on the right side of the face with that on the left side of the face on the basis of the criteria as shown in Table 3. The results of the evaluation were expressed in terms of the average scores in Table 4.

TABLE 3

| Criteria | Score |
|---|---|
| Compared with the control product: | |
| Completely healed | 4 |
| Apparently improved | 3 |
| Slightly improved | 2 |
| No difference | 1 |

TABLE 4

| Composition | Average Score |
|---|---|
| Formulation Example 1 | 3.0 ± 0.5 |
| Formulation Example 2 | 3.5 ± 0.3 |
| Formulation Example 3 | 3.1 ± 0.5 |
| Formulation Example 4 | 3.2 ± 0.3 |
| Formulation Example 5 | 3.6 ± 0.3 |

As Table 4 shows, the topical compositions according to the present invention clearly show therapeutic effects on acne vulgaris, even though the contents of the active ingredients are relatively small. In addition, none of the subjects suffered from any abnormality such as skin irritation.

The present invention makes it possible to inhibit proliferation of *Propionibacterium acnes*, which causes acne vulgaris, or kill the bacterium, to effectively treat or prevent acne vulgaris. Further, the present invention provides a topical composition for treating or preventing acne vulgaris which is excellent in safety.

While the invention has been described in detail and with reference to specific examples thereof, it will be apparent to one skilled in the art that various changes and modifications can be made therein without departing from the spirit and scope thereof.

What is claimed is:

1. A topical composition for treating or preventing acne vulgaris which comprises therein, as an active ingredient, in an amount effective to inhibit the growth of *Propionibacterium acnes*, at least one saturated or unsaturated chain alcohol having 18 carbon atoms represented by formula (1):

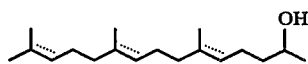
(1)

wherein a dotted line represents either the presence or the absence of a double bond, and at least one carrier or diluent acceptable for topical application.

2. The topical composition according to claim 1, wherein an amount of the active ingredient ranges from 0.005 to 0.5% by weight based on the total weight of the composition.

3. The topical composition according to claim 1, wherein an amount of the active ingredient ranges from 0.01 to 0.5% by weight based on the total weight of the composition.

4. A method of treating or preventing acne vulgaris which comprises topically applying to a patient a composition which comprises therein, as an active ingredient, in an amount effective to inhibit the growth of *Propionibacterium acnes*, at least one saturated or unsaturated chain alcohol having 18 carbon atoms represented by formula (1):

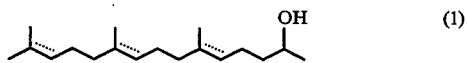
(1)

wherein a dotted line represents either the presence or the absence of a double bond, and at least one carrier or diluent acceptable for topical application.

5. The method according to claim 4, wherein the composition comprises from 0.005 to 0.5% by weight of the active ingredient.

6. The method according to claim 4, wherein the composition comprises from 0.01 to 0.5% by weight of the active ingredient.

* * * * *